United States Patent [19]

Bank et al.

[11] Patent Number: 6,114,680

[45] Date of Patent: Sep. 5, 2000

[54] METHOD FOR PROCESSING A SAMPLE

[75] Inventors: Petrus Cornelis Bank, Deventer; Adriaan Gerardus Snijders, Lochem, both of Netherlands

[73] Assignee: Perkin Elmer LLC, Norwalk, Conn.

[21] Appl. No.: 09/101,819

[22] PCT Filed: Jan. 7, 1997

[86] PCT No.: PCT/NL97/00005

§ 371 Date: Oct. 20, 1998

§ 102(e) Date: Oct. 20, 1998

[87] PCT Pub. No.: WO97/26064

PCT Pub. Date: Jul. 24, 1997

[30] Foreign Application Priority Data

Jan. 17, 1996 [NL] Netherlands .......................... 1002110

[51] Int. Cl.[7] ........................................... H05B 6/80
[52] U.S. Cl. .............................. 219/731; 219/762; 422/21
[58] Field of Search .................................. 219/731, 762; 392/441, 444; 99/451, 483; 422/21–24, 307, 3, 25, 41, 105, 108, 109, 112, 116, 119, 295, 299; 426/240, 241, 243; 435/173.2

[56] References Cited

U.S. PATENT DOCUMENTS

| | | |
|---|---|---|
| 3,489,526 | 1/1970 | El-Roy et al. . |
| 3,645,849 | 2/1972 | Gray ..................................... 435/173.2 |
| 4,979,896 | 12/1990 | Kinoshita . |
| 5,320,804 | 6/1994 | Zakaria et al. ............................. 422/21 |
| 5,368,171 | 11/1994 | Jackson . |
| 5,458,897 | 10/1995 | Paré . |
| 5,732,476 | 3/1998 | Pare ......................................... 34/265 |

FOREIGN PATENT DOCUMENTS

| | | |
|---|---|---|
| 0 467 625 | 1/1992 | European Pat. Off. . |
| 0 549 495 | 6/1993 | European Pat. Off. . |
| 0 595 084 | 5/1994 | European Pat. Off. . |
| 0 628 332 | 12/1994 | European Pat. Off. . |
| 2 674 146 | 9/1992 | France . |
| 44 19 648 | 9/1995 | Germany . |
| 1-104303 | 4/1989 | Japan . |

OTHER PUBLICATIONS

T. Lo et al., "Solvent Extraction", *Encyclopedia of Physical Science and Technology*, vol. 13, 1987, pp. 72–96.

H. Budzinski et al., "Extraction Assistée par Chauffage Micro–Ondes Focalisées (MOF) à Pression Ambiante des Composés Organiques dans les Martices Naturelles: Application à L'Analyse des Composés Aromatiques", *Comptes–Rendus de L'Academie Des Sciences*, vol. 321, No. 2, Jul. 1995, pp. 69–76.

J. Paré et al., "Microwave–Assisted Process (MAP™)$_a$: A New Tool for the Analytical Laboratory", *TrAC Trends in Analytical Chemistry*, vol. 13, No. 4, Apr. 1994, pp. 176–184.

*Primary Examiner*—Teresa Walberg
*Assistant Examiner*—Shawntina Fuqua
*Attorney, Agent, or Firm*—St. Onge Steward Johnston & Reens LLC

[57] ABSTRACT

A method for processing samples in a sealable container which is transparent to electromagnetic radiation, includes a) the sample and a polar non-solid medium being introduced into the container, b) the container being placed in a vessel which is transparent to electromagnetic radiation and which is filled with a nonpolar coolant which is transparent to electromagnetic radiation, and c) the vessel being irradiated with electromagnetic radiation, the temperature of the coolant being maintained lower than 5° C. and a vessel being used which is provided with an insulating material which is transparent to electromagnetic radiation.

25 Claims, 2 Drawing Sheets

METHOD FOR PROCESSING A SAMPLE

BACKGROUND OF THE INVENTION

The invention relates to a method for processing samples in a sealable container which is transparent to electromagnetic radiation, in which method;

a) the sample and a polar non-solid medium are introduced into the container.

b) the container is placed in a vessel which is transparent to electromagnetic radiation and which is filled with a nonpolar coolant which is transparent to electromagnetic radiation, and c) the vessel is irradiated with electromagnetic radiation.

A polar non-solid medium is understood as meaning a medium which is in the liquid state when it is used. It is therefore possible that the polar non-solid medium is in the solid state at fairly low temperatures, for example at room temperature, but the polar-non-solid medium becomes liquid at higher temperature.

DESCRIPTION OF THE RELATED ARTS

The French Patent Application 2,674,146 discloses a device which comprises a cylindrical outer container and a cylindrical inner container. The outer container comprises a vessel and a lid which are detachably joined to one another. The lid of the vessel is provided with a plunger which, when the lid and the vessel of the outer container are joined to one another and the inner container is placed in the outer container, seals the inner container. Both the inner container and the outer container are essentially transparent to microwaves and the outer container is resistant to high pressure. Furthermore, a space is present between the outer container and the inner container into which a coolant can be introduced. The coolant is preferably air, but can also be another gaseous or liquid substance, provided that said substance absorb has little or no microwave absorption. The device according to the French Patent Application 2,674,146 is said to be suitable, in particular, for heating substances under high pressure using microwaves. A disadvantage of said device is, however, that, if a coolant is used which is at a low temperature, for example solid carbon dioxide or liquid nitrogen, condensation of water vapour on the outside of the outer container will occur. This condensed water vapour will absorb microwave radiation during the heating, as a result of which the heating of the substances which are present in the inner container cannot be adequately effected.

It is known that samples, for example soil samples, often have to undergo a processing before the samples are suitable for chemical and physical analyses. Thus, soil samples, for example, are treated with a mixture of concentrated nitric acid and concentrated hydrochloric acid (aqua regia) to dissolve heavy metals present in the sample. Aqua regia is added to such samples and the mixture obtained in this way is heated for a certain time. The treatment is carried out by introducing the sample and the aqua regia into a sealable container which is transparent to microwave radiation. The mixture of the sample and the aqua regia is then heated by exposing the container to microwave radiation. Then the container has to be cooled and the sample has to be subjected to further treatment, such as weighing, decanting, filtering, centrifuging and diluting, after which the contents of heavy metals dissolved in the aqua regia are determined. A disadvantage is that the container has to be made of Teflon. It has been found that such containers have to be vigorously and thoroughly cleaned before re-use, in particular if the containers contain chemically aggressive substances, such as aqua regia.

SUMMARY OF THE INVENTION

The present invention has the intention of providing a solution to the problems and disadvantages cited above. The object of the invention is to provide a method for treating samples, in which method the container no longer has to be cooled after the small vessel has been exposed to microwave radiation. Another object of the present invention is to provide a method in which the further processing steps, such as weighing, diluting and the like, are no longer necessary. A further object of the present invention is to provide a method which can also be carried out on a small scale, as a result of which less chemical waste is produced. Still another object of the invention is that the method can be carried out in a relatively short time. The present invention therefore relates to a method for treating samples in a sealable container, such as that described above, in which method the temperature of the coolant is lower than 5° C. and a vessel is used which is provided with an insulating material which is transparent to electromagnetic radiation.

If a coolant at a low temperature is used, this has the advantage that during the heating of the sample and the polar non-solid medium no build-up of high pressures will occur since the heat of condensation can effectively be removed and substances which are in the gas phase can easily be returned again to the liquid or solid state, whereas the sample and the polar non-solid medium can be heated to a high temperature. This is advantageous, in particular, if the processing is carried out on a small scale using a device suitable therefor, as will be clear to the person skilled in the art.

According to the invention, the method is suitable for treating samples which have to undergo a heat treatment in the presence of a polar non-solid medium. It is also possible that the polar non-solid medium reacts with the sample or with one or more constituents thereof. Thus, for example, metals present in the sample may be reacted with a solution of an acid in water to form the corresponding salts. Examples of treatments in which samples undergo a heat treatment in the presence of a polar non-solid medium are heating with reflux cooling, distillation or (continuous) extraction.

According to the invention, all kinds of samples can be treated by the method. Examples of suitable samples are soil samples, samples of sediments, sludge, minerals, oil and oil products, biological samples, samples containing metals and/or ceramic materials, and water samples, for example samples of surface water.

The temperature of the coolant must be lower than the temperature of the mixture of the sample and of the polar non-solid medium. Preferably, the temperature of the coolant is at least 20° C., more preferably at least 35° C. and, in particular, at least 75° C. lower than the temperature of the mixture. Because the mixture will generally be at a temperature of approximately room temperature (approximately 25° C.) or higher, the temperature of the coolant is therefore at least lower than 5° C., preferably lower than −10° C. and, in particular, lower than −50° C.

According to the invention, the coolant must be essentially or completely transparent to electromagnetic radiation. The coolant therefore preferably has a dissipation factor of less than 10, in particular of less than 5.

The dissipation factor of a substance is understood as meaning the ratio of the lowering of the permittivity of the substance as a consequence of exposure to electromagnetic radiation, the lowering factor or loss factor $\epsilon''$ to the permittivity $\epsilon$ of the substance:

Dissipation factor=tan $\delta=\epsilon''/\epsilon$.

Here the lowering factor or loss factor $\epsilon''$ is a measure of the ability of the substance to dissipate the electromagnetic energy.

Examples of suitable coolants are liquid nitrogen, liquid argon and solid carbon dioxide. Suitable coolants can also be certain, generally nonpolar, organic substances which have been cooled to the desired temperature for the use thereof as coolant. Examples of such organic substances are alkanes and halogenated alkanes. According to the invention, a solid coolant, and in particular solid carbon dioxide, is preferably used.

According to the invention the polar non-solid medium may be a polar liquid or a mixture of different polar liquids. A polar liquid is understood here as meaning a liquid which has a permittivity $\epsilon$ at 25° C. of at least 2, preferably of more than 5, more preferably of more than 10 and, In particular, of more than 50. Suitable polar liquids may be inorgaic or organic substances. Examples of suitable polar liquids are acetone, ethanol, water, butanone, acetonitrile and certain oils and fats. Water, in particular, is used as the polar non-solid medium.

The polar non-solid medium may also be a mixture of one or more polar and nonpolar liquids. If the polar non-solid medium comprises a polar and a nonpolar liquid, such a medium will usually be a two-phase system. These two phases can be mixed, for example, by means of a stirring device. The mixing of a mixture of a polar and a nonpolar liquid can also be increased by a means suitable therefor, for example a dispersant or a phase-trafer catalyst, such as hexadecylammonium bromide.

The polar non-solid medium may contain additives which are possibly dissolved in the medium. Said additives may be chemical substances which react with the sample or with one or more constituents thereof. Thus, the additives may be acids which react with metals to form the corresponding salts. The additives may also be dispersants or emulsifiers or other substances which increase the dissolution, dispersion or emulsification of the sample or of one or more constituents thereof in the medium. Examples of such agents are monoesters and diesters of glycerol and fatty acids having long chains or monoesters of glycol and fatty acids having long chains, detergents such as alkyl sulphonates or alkyl ethoxylates and phase-transfer catalysts such as hexadecylammonium bromide.

According to the invention, the polar non-solid medium may also be a polar liquid which may be in the superheated state. Under the influence of microwave radiation, a liquid can be heated at atmospheric pressure to a temperature which is higher than the boiling point of the liquid at atmospheric pressure. Thus, it has been found that, with the aid of microwave radiation, water can be heated at atmospheric pressure to a temperature of approximately 105° C. and acetonitrile even to a temperature of approximately 120° C.

According to the invention, the polar non-solid medium may also be a polar substance which may be in the supercritical state. The polar non-solid medium may also comprise one or more polar and nonpolar substances which may be in the supercritical state. According to the invention, substances can advantageously be used which have a critical temperature of up to 200° C. and a permittivity $\epsilon$ of at least 5 at 25° C. Preferably, such substances have a critical temperature of approximately 0° to approximately 150° C. Examples of such suitable polar substances ame dimethyl ether, fluoromethane and monochlorodifluoromethane. Although chlorofluorohydrocarbons such as monochlorodifluoromethane are suitable coolants, these substances are, however, less preferred because of their supposed disadvantageous effects an the environment. Examples of suitable nonpolar substances are carbon dioxide ad pentane, According to the present invention, the polar non-solid medium is preferably chosen from the group comprising polar liquids and polar substances which can be in the superheated or supercritical state.

It will be clear that the container has to be filled with a certain quantity of the polar non-solid medium. Preferably, the container is not, however, completely filled. According to the present invention, the container is therefore advantageously filled with a quantity of 10 to 90% by volume of the mixture of the sample and the polar non-solid medium, in particular with a quantity of 20 to 40% by volume.

According to the invention, electromagnetic radiation can he used which falls within the frequency range of radio waves having an ultra-high frequency and microwaves. The frequency of the electromagrnetic radiation is therefore, according to the invention, preferably between 3 MHz and 30 GHz, in particular between 30 MHz and 3 GHz.

Before the sample is processed according to the method of the present invention, the sample and the polar non-solid medium are advantageously mixed for at least 15 minutes and preferably for at least 30 minutes in the container using a vortex stirring device so that pressure build-up and foam formation will occur to a lesser extent during the processing of the samples by the method according to the present invention.

The method according to the present invention is suitable, in particular, for processing samples in this way which contain heavy metals, said heavy metals being dissolved with the aid of an acid, for example a mixture of concentrated nitric acid and concentrated hydrochloric acid.

The invention also relates to a device for processing samples, which comprises a source of electromagnetic radiation, a vessel for a coolant, which vessel is transparent to electromagnetic radiation and a sealable container, the source of electromagnetic radiation being placed outside the container and the container being placed inside the coolant and the vessel being provided with an insulating material which is transparent to electromagnetic radiation.

As described above, if a coolant is used at a low temperature, it is necessary to use a vessel which is provided with an insulation material so that condensation of water vapour on the wall of the vessel will not occur and heating of the sample and the polar non-solid medium can take place efficiently in the container.

DESCRIPTION OF THE PREFERRED EMBODIMENTS

Figure 1:
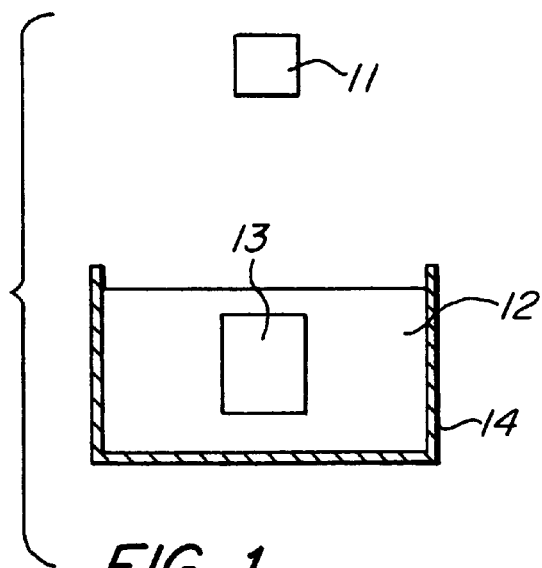
FIG. 1 shows an embodiment of the inventive apparatus.

FIG. 1 shows an embodiment of the device according to the invention. Said embodiment comprises a source of electromagnetic radiation 11, a coolant 12 which is transparent to electromagnetic radiation, a sealable container 13 and a vessel 14 which is transparent to electromagnetic radiation and which is provided an the outside with an insulation material which is transparent to electromagnetic radiation. It will be clear that the vessel can be composed largely or completely of an insulation which is transparent to electromagnetic radiation.

The source of electromagnetic radiation is placed outside the container and the container is placed inside the coolant. It is therefore possible that a source of electromagnetic radiation is used which is situated outside the container, but inside the vessel. A source of electromagnetic radiation can also be used with the source being placed outside the vessel, provided that a vessel is used which is essentially transparent to electromagnetic radiation.

Preferably, the source of electromagnetic radiation provides radiation having a frequency of 3 MHz to 30 GHz, in particular of 30 MHz to 3 GHz.

The vessel 14 is provided with an insulating material so that condensation of water vapour is prevented from taking place on the wall of the vessel. It will be clear that the insulating material must be essentially transparent to electromagnetic radiation if the source of electromagnetic radiation is placed outside the vessel. The insulating material must also have suffficient insulating power to keep the coolants sufficiently cool, said coolants being optionally enclosed by a vessel, even if the temperature of the coolants is very low. According to the invention, the insulating material preferably has a thermal conductivity of at most 0.1 $W.m^{-1}.K^{-1}$ at 24° C. and a dissipation factor of less than 100. Suitable insulating materials are plastics, for example expanded polystyrene and polyurethane foam, glass wool, rock wool and certain ceramic materials, for example porcelain, alumina and cordenite.

The container 13 is advantageously resistant to aggressive chemical substances, such as strong acids and bases. The container is therefore advantageously made of an essentially chemically inert material. The material of which the container is made should also essentially be transparent to electromagnetic radiation. Suitable materials are, for example, ceramic materials, glass and plastics. Suitable ceramic materials are porcelain, alumina and cordenite. Suitable types of glass are quartz, flint glass, pyrex and borosilicate. Suitable plastics are, for example, poly (tetrafluoroethene), polypropene, polystyrene, poly (sulphone), polyethene, polypropene, acrylamide/butadiene/styrene terpolymers and polycarbonate. The plastics may optionally be reinforced with fibres, for example fibre-reinforced epoxy resins. Examples of suitable fibres are glass fibres, carbon fibres and aramid fibres.

The container may optionally be made in such a way that it can withstand high and low pressures, for example pressures of $10^{-6}$ mbar to 150 bar. In addition, either an open container or a sealed container can be used.

The device according to the invention can also be provided with means for measuring and regulating the temperature of the mixture of the sample and the polar non-solid medium. Optionally, the device also comprises a means of measuring and regulating the pressure in the sealable container. The device is advantageously provided with a means which regulates the power of the source of electromagnetic radiation. It will be clear that the device may be provided with more than one source so that electromagnetic radiation having different frequencies can be supplied. It is very advantageous if the device according to the invention is provided with a means which regulates the power and optionally the frequency of the electromagnetic radiation on the basis of the desired temperature of the polar non-solid medium.

According to the invention, the container may have diverse shapes. A preferred embodiment of the container is shown in, FIG. 2. The container 21 shown there is tubular and is provided at the top with a sealing means 22. The dimensions of the container are preferably: height 0.5 to 50 cm, cross section 0.3 to 10 cm. The means 22 may seal the container 21 by means of a screw joint, for example a screw thread joint or a so-called bayonet catch, or a quick-acting or snap joint. The means 22 may also be provided with a means on which a supply device can be mounted by means, for example, of a screw thread joint. The means 22 may also comprise a means through which the supply device can be provided, for example a septum, through which an injection needle can be inserted. Such an embodiment of a device according to the invention is suitable, in particular, for carrying out chemical reactions because one or more reagents can be added while the method according to the invention is being carried out.

Figure 2:
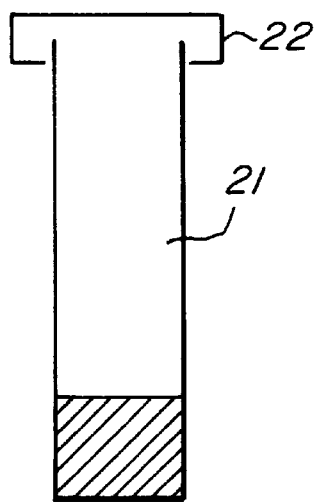
FIGS. 2 and 3 show embodiments of the container.

The preferred embodiment according to FIG. 2 may also be provided with a material which is essentially opaque to electromagnetic radiation so that only the sample and the polar non-solid medium can be exposed to electromagnetic radiation in the course of the method according to the invention. The material which is essentially opaque to electromagnetic radiation is therefore mounted on the outside and/or the inside of the wall of the container in such a way that the material which is essentially opaque to electromagnetic radiation is mounted between means 22 and the level of the sample and the polar non-solid medium. In this connection, it is, however, necessary for the length of the material which is essentially opaque to electromagnetic radiation not to be such that it can act as an aerial for the electromagnetic radiation. The length of the material should therefore not be equal to a whole multiple of the half wavelength of the electromagnetic radiation.

Preferably, the material which is opaque to electromagnetic radiation contains one or more metals and said material is, in particular, an aluminium-containing foil.

Figure 3:
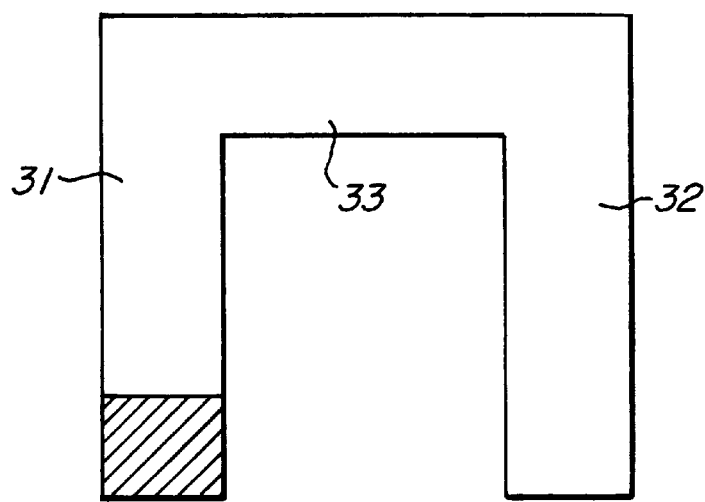

Another preferred embodiment of the container is shown in FIG. 3. Said preferred embodiment is a so-called (inverted) u-shape and comprises two upright tubular parts 31 and 32, the upright tubular parts being joined by a transversely situated tubular part 33. The various parts may optionally be separable. The dimensions of said preferred embodiment are: height 0.5 to 50 cm, width 0.5 to 25 cm, cross section of the parts 31–33 0.3 to 10 cm. The container is optionally also provided with one or more sealable openings for filling and emptying it. Such an embodiment of the container is suitable, for example, for carrying out a distillation. In this connection, for example, tubular part 31 is filled with a mixture of liquids and the container is placed in the coolant. Then the container is irradiated in such a way that only the tubular part 31 is exposed to electromagnetic radiation, as a result of which vapour of the most volatile liquid(s) will condense in the tubular part 32. It will be clear that the partial irradiation of the container can be carried out when the entire container is exposed to electromagnetic radiation, the tubular part 32 being shielded by a material which essentially transmits no electromagnetic radiation, said material preferably being the same as the material which is essentially opaque to electromagnetic radiation and which can be used in the exemplary embodiment according to FIG. 2.

It goes without saying that a container can also be used which is an assembly of more tubular parts and one or more parts may be straight or curved. It is therefore possible to use containers which have a complex geometry. Examples of such containers which have complex geometry are comparable with apparatuses for carrying out extractions and distillations, for example a soxhlet extraction apparatus (solid/liquid extraction).

The container can be exposed to electromgnetic radiation in such a way that only some of the coolant or of the vessel containing the coolant is irradiated. A container will advantageously be only partially exposed to electromagnetic radiation if it comprises more tubular parts, in particular if a container is used which is suitable, for example, for continuous extraction.

Figure 4:
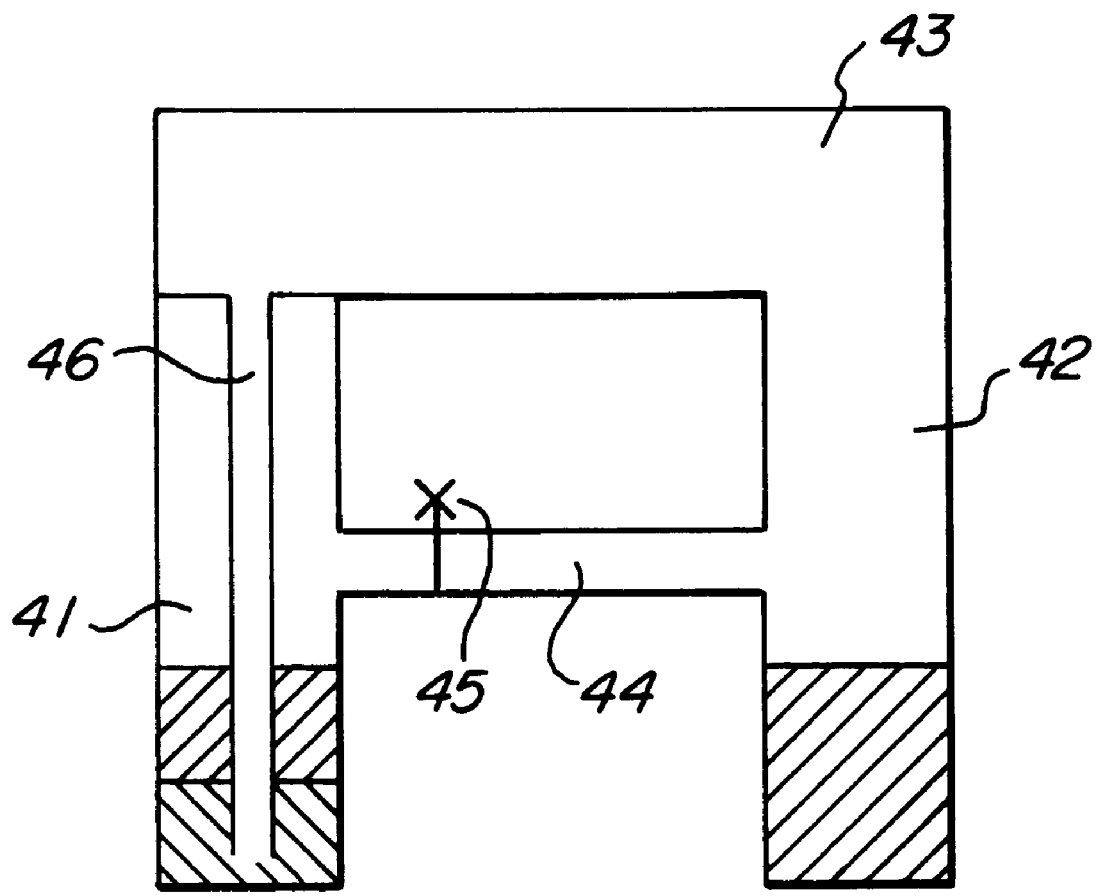
FIG. 4 is a diagammatic example of an embodiment.

A diagrammatic example of such an embodiment, which is optionally separable, for carrying out a continuous extraction is shown in FIG. 4. Said embodiment comprises two upright tubular parts 41 and 42 and two transversely situated parts 43 and 44, part 44 being provided with a sealing means 45. In this case, part 44 acts as a siphon. Part 41 also comprises a tube 46. Such an embodiment can, for example, be used as follows. Part 41 is filled with a mixture of a suitable polar liquid which contains substances which it is desired to extract, and a suitable nonpolar liquid, the nonpolar liquid having a lower density than the polar liquid. Part 41 is filled with the mixture to a level below that of part 44 so that the tube 46 projects into the polar liquid. Part 42 is filled with the nonpolar liquid to a level below that of part 44. The container is placed in the coolant.

The operation of this embodiment is as follows. If part 42 is exposed to electromagnetic radiation, nonpolar liquid will evaporate and condense in part 41, as a result of which nonpolar liquid is passed through the polar liquid via tube 46. During the process, the level of the nonpolar liquid rises in part 41. Ultimately, the level reaches the height of, or higher than, part 44, as a result of which some of the nonpolar liquid containing the extracted substances can be siphoned back into part 42 by opening sealing means 45. Ultimately, almost all the extracted substances will be contained in part 42. After completing the continuous extraction, the content of part 41, i.e. the combination of the polar liquid and some of the nonpolar liquid may optionally be separated in order to obtain the last residues of substances to be extracted.

The invention will be explained further by reference to an example.

EXAMPLE I

In this example, two methods for preparing the sample (digestion) are described, method A corresponding to the method according to the invention and method B and C Comprising a standard procedure.

The contents of different metals (cadmium, chromium, copper, nickel, lead, zinc, arsenic and mercury) in different soil samples are determined by treating the soil samples with a mixture of nitric acid and hydrochloric acid and then analysing the dissolved salts of said metals with the aid of ICP.

Method A (according to the invention; derived from NVN 5770):

A quantity of 0.15 to 0.4 g of visually homogeneous samples having a content of solids of more than 50% by weight was weighed out with an accuracy of 0.0001 g into a disposable polypropylene conical-bottom tube (14 ml, 17×200 mm). Then 1.9 ml of a hydrochloric acid solution prepared by adding 50 ml of demineralized water to 2.5 l of concentrated hydrochloric acid (12 mol HCl per litre), and 0.6 ml of a nitric acid solution (15 mol of $HNO_3$ per litre) were added to the weighed quantities of the samples. The conical-bottom tube was then sealed with a screw lid.

The conical-bottom tubes were shaken with the aid of a vortex stirring device until carbon dioxide no longer escaped and/or other visible reactions no longer took place; it is found that shaking for at least 30 minutes is generally adequate.

In a subsequent step, 10 conical-bottom tubes were placed with a gap of at least 1 cm in an expanded polystyrene tray completely filled with solid carbon dioxide in such a way that the conical-bottom tubes were clear of each other and clear of the wall of the tray. The tray was then sealed with a lid.

The tray was then placed in a microwave oven (MDS 2000 from CEM Corporation) and subjected to the following program;

Power: 23%

Time: 60 minutes

Fan speed; 100 rpm.

After removing them from the tray, the tubes were allowed to cool to room temperature and 11.5 ml of demineralized water was added to each tube, a final volume of 14.0 ml being obtained.

The content of the conical-bottom tubes was homogenized and the solid material was allowed to settle or the tubes were centrifuged.

Then a 1.0 ml sample was taken from the conical-bottom tubes for analysis for mercury, said sample being introduced into a 12 ml conical-bottom tube (17×150 mm). Then 9.0 ml of demineralized water was added and the content of the conical-bottom tube was homogenized.

Method B (comparative):

This method was carried out in accordance with the standardized method NEN 6465 and comprises a digestion using a conventional laboratory set-up (reflux condenser).

Method C (comparative):

This method was carried out in accordance with the standardized method NVN 5770, the digestion being carried out in a Teflon vessel using microwaves.

The quantities of cadmium, chromium, copper, nickel, lead, zinc, arsenic and mercury in the samples pretreated according to method A, B or C were determined with the aid of ICP. The results were evaluated with the aid of a statistical test [Wilcoxon-T test; D. L. Massart, B. G. M. Vandeginste et al., "Chemometrics: A Textbook", Vol. 2, "Data Handling in Science and Technology", pages 57–58 (1988)]. This test is a two-sided check for the differences in paired observations. having an uncertainty of 0.05.

From the results of this test, a quantitative evaluation can be drawn up which is shown in the table below, the degree of certainty being indicated by evaluation FIGS. 1–5. In this connection, the evaluation FIG. 1 indicates a low certainty and the evaluation FIG. 5 a high certainty. A difference between two evaluation figures of 2 or more is statistically significant. An evaluation figure of 1 is assigned to the least certain method, the evaluation figures of other methods being increased by 1 (more reliable, not statistically significant) or by or more (more reliable, statistically significant).

|    | Method A | Method B | Method C |
| --- | --- | --- | --- |
| Cd | 4 | 3 | 1 |
| Cr | 3 | 5 | 1 |
| Cu | 2 | 2 | 1 |
| Ni | 2 | 3 | 1 |
| Pb | 3 | 1 | 2 |
| Zn | 2 | 4 | 1 |
| As | 3 | 1 | 2 |
| Hg | 4 | 1 | 3 |

From the above table it is apparent that the comparative method C yields the least reliable results for the elements cadmium, chromium, copper, nickel and zinc. The least reliable results are obtained by method B for the elements lead, arsenic and mercury. The method according to the invention (method A) therefore yields the most reliable result for the series of elements which are shown in the above table so that this method is preferable for such an analysis. A further advantage of the method according to the invention is that simple equipment and only small quantities of various chemicals are needed.

What is claimed is:

1. Method for processing samples in a sealable container which is transparent to electromagnetic radiation, in which method:
   a) the sample and a polar liquid medium are introduced into the container,
   b) the container is placed in a vessel which is transparent to the electromagnetic radiation and which is filled with a nonpolar coolant which is transparent to the electromagnetic radiation, and
   c) the vessel is irradiated with electromagnetic radiation, wherein the frequency of the electromagnetic radiation is between 3 MHz and 30 GHz,
   wherein the temperature of the coolant is maintained lower than 5° C. to provide for condensation of gaseous products formed in the container upon heating and
   wherein a vessel is used which is provided with an insulating material which is transparent to the electromagnetic radiation.

2. Method according to claim 1, wherein the liquid coolant has a dissipation factor of less than 10.

3. Method according to claim 1, wherein the coolant is a solid coolant.

4. Method according to claim 3, wherein the coolant is solid carbon dioxide.

5. Method according to claim 4, wherein the polar liquid medium is chosen from the group comprising polar liquids and polar substances which are in the supercritical state.

6. Method according to claim 1, wherein the container is filled with a quantity of 10–99% by volume of the mixture of the sample and the polar liquid medium.

7. Method according to claim 1, wherein the container is filled with a quantity of 20–40% by volume of the mixture of the sample and the polar liquid medium.

8. Method according to claim 1, wherein a U-shaped container is used which comprises two upright tubular parts which are joined by a transversely situated tubular part wherein the tubular parts are optionally separable.

9. Method according to claim 1, wherein the coolant is irradiated with electromagnetic radiation in such a way that only a part of the container is exposed to electromagnetic radiation.

10. Method according to claim 1, wherein a container is used which is provided with a material which is opaque to electromagnetic radiation in such a way that, in step c), only the sample and the polar liquid medium are exposed to electromagnetic radiation.

11. Method according to claim 10, wherein a length of the material which is essentially opaque to electromagnetic radiation is not equal to a whole multiple of the half wavelength of the electromagnetic radiation.

12. Method according to claim 10, wherein the material which is opaque to electromagnetic radiation contains one or more metals.

13. Method according to claim 12, wherein the material which is opaque to electromagnetic radiation is an aluminium-containing foil.

14. Method according to claim 1, wherein only that part of the container is cooled which is in contact with the sample and the polar liquid medium.

15. Device for processing samples, which comprises a source of electromagnetic radiation wherein the source of electromagnetic radiation supplies radiation at a frequency of 3 MHz to 30 GHz, a vessel for a coolant, which vessel is transparent to electromagnetic radiation, and a sealable container, the source of electromagnetic radiation being placed outside the container and the container being placed inside the coolant, the vessel is provided with an insulating material which is transparent to electromagnetic radiation.

16. Device according to claim 15, wherein the thermal conductivity of the insulating material is at most 0.1 $W.m^{-1}.K^{-1}$ at 24° C.

17. Device according to claim 15, wherein the dissipation factor of the insulating material is less than 100.

18. Device according to claim 15, wherein the container is provided with a material which is essentially opaque to electromagnetic radiation in such a way that, if the container contains a sample and a polar liquid medium, only the sample and the polar liquid medium can be exposed to electromagnetic radiation.

19. Device according to claim 18, wherein the length of the material which is essentially opaque to electromagnetic radiation is not equal to a whole multiple of the half wavelength of the electromagnetic radiation.

20. Device according to claim 19, wherein the material which is opaque to electromagnetic radiation contains one or more metals.

21. Device according to claim 20, wherein the material which is opaque to electromagnetic radiation is an aluminium-containing foil.

22. Device according to claim 15, wherein the container is made of a chemically inert material.

23. Device according to claim 15, wherein the chemically inert material may be a ceramic material, glass or a plastic.

24. Device according to claim 15, wherein the container is a u-shaped container comprising two upright tubular parts which are joined by a transversely situated tubular part, wherein the tubular parts are optionally separable.

25. Method of claim 1, wherein said step of placing a container in a vessel, places a container without a separate reinforcement means for resisting high pressures with the container.

* * * * *